(12) United States Patent
Olbrich et al.

(10) Patent No.: US 10,407,489 B2
(45) Date of Patent: Sep. 10, 2019

(54) METHOD FOR THE PRODUCTION OF FREEZE-DRIED PELLETS COMPRISING FACTOR VIII

(71) Applicant: Bayer Pharma Aktiengesellschaft, Berlin (DE)

(72) Inventors: Carsten Olbrich, Berlin (DE); Matthias Plitzko, Neuenburg (DE); Bernhard Luy, Freiburg (DE); Stefan Christian Schneid, Düsseldorf (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 15/775,730

(22) PCT Filed: Nov. 4, 2016

(86) PCT No.: PCT/EP2016/076640
§ 371 (c)(1),
(2) Date: May 11, 2018

(87) PCT Pub. No.: WO2017/080915
PCT Pub. Date: May 18, 2017

(65) Prior Publication Data
US 2018/0327478 A1 Nov. 15, 2018

(30) Foreign Application Priority Data
Nov. 12, 2015 (EP) .................................... 15194340

(51) Int. Cl.
*A61K 9/19* (2006.01)
*C07K 14/755* (2006.01)
(Continued)

(52) U.S. Cl.
CPC .............. *C07K 14/755* (2013.01); *A61K 9/19* (2013.01); *F26B 5/065* (2013.01); *F26B 11/04* (2013.01); *F26B 11/049* (2013.01)

(58) Field of Classification Search
CPC ........ A61K 9/19; C07K 14/755; C08K 13/02; F26B 11/04; F26B 11/049; F26B 5/065
See application file for complete search history.

(56) References Cited

U.S. PATENT DOCUMENTS

| 4,757,006 A | 7/1988 | Toole, Jr. et al. |
| 4,868,112 A | 9/1989 | Toole, Jr. |

(Continued)

FOREIGN PATENT DOCUMENTS

| EP | 306968 | 3/1989 |
| EP | 2578975 | 4/2013 |

(Continued)

OTHER PUBLICATIONS

Andersson, L., et al., (May 1986) Isolation and characterization of human factor VIII: Molecular forms in commercial factor VIII concentrate, cryoprecipitate, and plasma, Medical Sciences, *Proc. Natl. Acad. Sci. USA*, 83:2979-2983.

(Continued)

*Primary Examiner* — Ernst V Arnold
(74) *Attorney, Agent, or Firm* — Morrison & Foerster LLP

(57) ABSTRACT

A method for the production of freeze-dried pellets comprising factor VIII comprises the steps of: a) freezing droplets of a solution comprising factor VIII to form pellets; b) freeze-drying the pellets; wherein in step a) the droplets are formed by means of droplet formation of the solution comprising factor VIII into a cooling tower which has a temperature-controllable inner wall surface and an interior temperature below the freezing temperature of the solution (Continued)

and wherein in step b) the pellets are freeze-dried in a rotating receptacle which is housed inside a vacuum chamber.

10 Claims, 7 Drawing Sheets

(51) Int. Cl.
*F26B 5/06* (2006.01)
*F26B 11/04* (2006.01)

(56) References Cited

U.S. PATENT DOCUMENTS

| | | | |
|---|---|---|---|
| 5,198,349 | A | 3/1993 | Kaufman |
| 5,250,421 | A | 10/1993 | Kaufman et al. |
| 5,733,873 | A | 3/1998 | Österberg et al. |
| 5,919,766 | A | 7/1999 | Österberg et al. |
| 2012/0167405 | A1 | 7/2012 | Hubbard, Jr. et al. |
| 2014/0373383 | A1* | 12/2014 | Struschka ............ F26B 5/06 34/287 |

FOREIGN PATENT DOCUMENTS

| | | |
|---|---|---|
| WO | WO2006/008006 | 1/2006 |
| WO | WO2009/020434 | 2/2009 |
| WO | WO2010/054238 | 5/2010 |
| WO | WO2013/050156 | 4/2013 |
| WO | WO2013/050161 | 4/2013 |

OTHER PUBLICATIONS

European Search Report dated Mar. 16, 2016 for European Application No. 15194340.4, filed Nov. 12, 2015, 5 pages.

International Search Report and Written Opinion dated Dec. 14, 2016 for International Application No. PCT/EP2016/076640, 9 pages.

Wang, D. Q., et al., (2010) "Process Robustness in Freeze Drying of Biopharmaceuticals," *Formulation of Process Development Strategies for Manufacturing Biopharmaceuticals*, Chapter 32 pp. 827-837.

* cited by examiner

METHOD FOR THE PRODUCTION OF FREEZE-DRIED PELLETS COMPRISING FACTOR VIII

CROSS REFERENCE TO RELATED APPLICATIONS

This application is a National Phase application under 35 U.S.C. § 371 of International Application No. PCT/EP2016/076640, filed Nov. 4, 2016, which claims priority benefit of European Application No. 15194340.4, filed Nov. 12, 2015.

FIELD OF THE INVENTION

The present invention relates to a method for the production of freeze-dried pellets comprising factor VIII, the method comprising the steps of: a) freezing droplets of a solution comprising factor VIII to form pellets; and b) freeze-drying the pellets.

BACKGROUND

Factor VIII (FVIII) is a protein found in blood plasma, which acts as a cofactor in the cascade of reactions leading to blood coagulation. A deficiency in the amount of FVIII activity in the blood results in the clotting disorder known as hemophilia A, an inherited condition primarily affecting males. Hemophilia A is currently treated with therapeutic preparations of FVIII derived from human plasma or manufactured using recombinant DNA technology. Such preparations are administered either in response to a bleeding episode (on-demand therapy) or at frequent, regular intervals to prevent uncontrolled bleeding (prophylaxis).

A conventional process for manufacturing and packaging parenteral biopharmaceuticals involves the formulation of a bulk solution in accordance with the measured biological activity of the intermediate material used to formulate the bulk solution. In many cases, particularly at the end of the process, the bulk solution is frozen and stored for making the assay. For this purpose the frozen solution may be stored for several days or even for several weeks. For the subsequent filling of the final packages, such as vials, for distribution to the end users, the frozen intermediate solution is typically thawed, bulked and filled into vials, and then freeze-dried within the vials.

The amount of thawed bulk solution that is filled into the final packaging vials is calculated on the basis of the assay of the intermediate solution. This calculation usually incorporates a large safety margin because of (1) large variation of biological assay and (2) loss of yield in the subsequent sterile fill and freeze-drying process. The loss of yield is due to product stress during this first freezing, storing and thawing step and the following second filling, freezing and drying process. This calculation is of course very difficult and based on product dependent empirical knowledge of the complete process.

In conventional processes the freeze-drying is usually performed in standard freeze drying chambers which do not have temperature controlled walls. These dryers, unfortunately, provide non-homogeneous heat transfer to the vials placed in the dryer chamber. Especially those vials which are positioned at the edges exchange energy more intensively than those positioned in the center of the plates, due to radiant heat exchange and natural convection in the gap between the wall of the chamber and the stack of plates/shelves. This non-uniformity of energy distribution leads to a variation of freezing and drying kinetics between the vials at the edges and those in the center, and could result in variation in the activities of the active contents of the respective vials. To ensure the uniformity of the final product, it is necessary to conduct extensive development and validation work both at laboratory and production scales.

The publication by Wang, D. Q., MacLean, D. and Ma, X. (2010) entitled Process Robustness in Freeze Drying of Biopharmaceuticals, in Formulation and Process Development Strategies for Manufacturing Biopharmaceuticals (eds F. Jameel and S. Hershenson), John Wiley & Sons, Inc., Hoboken, N.J., USA discloses specific freeze-drying cycles for recombinant FVIII but still acknowledges potency variations as a function of the vial position in the freeze-drying chamber.

WO 2010/054238 A1 reports on a stable lyophilized pharmaceutical formulation of Factor VIII (FVIII) comprising: (a) a FVIII; (b) one or more buffering agents; (c) one or more antioxidants; (d) one or more stabilizing agents; and (e) one or more surfactants; said FVIII comprising a polypeptide selected from the group consisting of: a) a recombinant FVIII polypeptide; b) a biologically active analog, fragment or variant of a); said buffer is comprising of a pH buffering agent in a range of about 0.1 mM to about 500 mM and said pH is in a range of about 2.0 to about 12.0; said antioxidant is at a concentration of about 0.005 to about 1.0 mg/ml; said stabilizing agent is at a concentration of about 0.005 to about 20%; said surfactant is at a concentration of about 0.001% to about 1.0%; and said formulation excluding sodium chloride (NaCl) or including only trace amount of NaCl.

WO 2006/008006 A1 is concerned with a process for sterile manufacturing, including freeze-drying, storing, assaying and filling of pelletized biopharmaceutical products in final containers such as vials. A process for producing containers of a freeze-dried product is disclosed, the process comprising the steps of freezing droplets of the product to form pellets, freeze-drying the pellets, assaying the freeze-dried pellets and loading the freeze-dried pellets into containers. More specifically, the process comprises the steps of: a) freezing droplets of the product to form pellets, whereby the droplets are formed by passing a solution of the product through frequency assisted nozzles and pellets are formed from said droplets by passing them through a counter-current flow of cryogenic gas; b) freeze-drying the pellets; c) storing and homogenizing the freeze-dried pellets; d) assaying the freeze dried pellets while they are being stored and homogenized; and e) loading the freeze-dried pellets into said containers.

WO 2013/050156 A1 describes a process line for the production of freeze-dried particles under closed conditions comprising at least a spray chamber for droplet generation and freeze congealing of the liquid droplets to form particles and a bulk freeze-dryer for freeze drying the particles, the freeze-dryer comprising a rotary drum for receiving the particles. Further, a transfer section is provided for a product transfer from the spray chamber to the freeze-dryer. For the production of the particles under end-to-end closed conditions each of the devices and of the transfer section is separately adapted for operation preserving sterility of the product to be freeze-dried and/or containment.

WO 2013/050161 A1 discloses a process line for the production of freeze-dried particles under closed conditions, the process line comprising a freeze-dryer for the bulk ware production of freeze-dried particles under closed conditions, the freeze-dryer comprising a rotary drum for receiving the frozen particles, and a stationary vacuum chamber housing the rotary drum, wherein for the production of the particles under closed conditions the vacuum chamber is adapted for closed operation during processing of the particles. The drum is in open communication with the vacuum chamber and at least one transfer section is provided for a product transfer between a separate device of the process line and the freeze-dryer, the freeze-dryer and the transfer section being separately adapted for closed operation, wherein the transfer section comprises a temperature-controllable inner wall surface.

SUMMARY OF THE INVENTION

According to some embodiments, a method is provided to produce freeze-dried pellets of factor VIII with fewer variations in activity for the individual pellets under conditions of strict separation from the outside - this includes any cryogenic gas such as liquid nitrogen.

In some embodiments, a method for the production of freeze-dried pellets comprising factor VIII is provided, the method comprising the steps of:
a) freezing droplets of a solution comprising factor VIII to form pellets;
b) freeze-drying the pellets;
wherein in step a) the droplets are formed by means of droplet formation of the solution comprising factor VIII into a cooling tower which has a temperature-controllable inner wall surface and an interior temperature below the freezing temperature of the solution and in step b) the pellets are freeze-dried in a rotating receptacle which is housed inside a vacuum chamber.

An operating principle of a method according to some embodiments has three distinct advantages. Firstly, it should be noted that in the method according to some embodiments, the sprayed droplets of the factor VIII-comprising solution do not contact a cryogenic gas in a counter-flow fashion such as described in WO 2006/008006 A1. There is no need for introducing a cryogenic gas into the interior space of the cooling tower and hence all handling and sterilization steps for the cryogenic gas can be omitted.

Secondly, by conducting the freeze-drying step in a rotating receptacle inside the vacuum chamber the spatial position of each individual pellet is evenly distributed over time. This ensures uniform drying conditions and therefore eliminates spatial variations of the activity of factor VIII as would be the case for freeze-dried vials on a rack.

Thirdly, it was experimentally found that pellets produced according to some embodiments display lesser microcollapses due to the overall process conditions that the FVIII polypeptides are exposed to in average being milder than those of the prior art. Said decreased occurrence of microcollapses of the pellets is visible in REM-pictures of such pellets that display a more homogenous surface, which again results in improved handling properties in later process steps for those pellets.

Direct comparison with the process as to the disclosure WO 2006/008006 A1 surprisingly showed that the surface morphology of the resulting pellets according to some embodiments is significantly more homogenous than the surface morphology of those pellets derived from the WO 2006/008006 A1 process; and the process according to some embodiments produces pellets with a further increased specific (BET-) surface, while those pellets of the WO 2006/008006 A1 process already had an improved homogeneity and specific surface compared to any Lyophilization processes known from the prior art.

It has been experimentally found that actual potencies of the pellets after freeze-drying are between 86.2% and 89.9% of the target potencies for factor VIII.

All steps of the method according to some embodiments can be carried out under sterile conditions and without compromising sterility between the individual steps.

Creation of frozen pellets can be performed with any of the known technologies, such as with a "Encapsulator Research" from Inotech Encapsulation, Switzerland, or "Kryogen Rapid Pelletizer" from Messer-Griesheim, Germany or "CRYOGENIC PELLETIZER" from IQFCRYO-GRAN, Canada. These prior art techniques however mostly rely on dropping droplets into liquid nitrogen to therein form pellets after drying off Due to the subsequent freeze drying step, the frozen pellets are expected to have a narrow particle size. Afterwards the frozen pellets can be transported under sterile and cold conditions to a freeze dryer. The pellets are then distributed across the carrying surfaces inside the drying chamber by the rotation of the receptacle. Sublimation drying is in principle possible in any kind of freeze dryers suited for pellets. Freeze dryers providing space for sublimation vapor flow, controlled wall temperatures and suitable cross sectional areas between drying chamber and condenser are preferred.

Details of the factor VIII variants which can be employed in the method according to some embodiments are described below. Preferably, a recombinant factor VIII derived from baby hamster kidney cells without additional proteins present is used.

which has at least a portion of the B domain intact, and which exhibits biological activity that is associated with native FVIII. In one embodiment of the disclosure, the FVIII molecule is full-length FVIII. The FVIII molecule is a protein which is encoded for by DNA sequences capable of hybridizing to DNA encoding FVIILC. Such a protein may contain amino acid deletions at various sites between or within the domains A1-A2-B-A3-C1-C2 (U.S. Pat. No. 4,868,112). The FVIII molecule may also be an analog of native FVIII wherein one or more amino acid residues have been replaced by site-directed mutagenesis.

According to the present disclosure, the term "recombinant Factor VIII " (rFVIII) may include any rFVIII, heterologous or naturally occurring, obtained via recombinant DNA technology, or a biologically active derivative thereof. In certain embodiments, the term encompasses proteins as described above and nucleic acids, encoding a rFVIII of the disclosure. Such nucleic acids include, for example and without limitation, genes, pre-mRNAs, mRNAs, polymorphic variants, alleles, synthetic and naturally-occurring mutants. Proteins embraced by the term rFVIII include, for example and without limitation, those proteins and polypeptides described hereinabove, proteins encoded by a nucleic acid described above, interspecies homologs and other polypeptides that: (1) have an amino acid sequence that has greater than about 60%, about 65%, about 70%, about 75%, about 80%, about 85%, about 90%, about 91%, about 92%, about 93%, about 94%, about 95%, about 96%, about 97%, about 98% or about 99% or greater amino acid sequence identity, over a region of at least about 25, about 50, about 100, about 200, about 300, about 400, or more amino acids (up to the full length sequence of 2332 amino acids for the mature native protein), to a polypeptide encoded by a referenced nucleic acid or an amino acid sequence described herein; and/or (2) specifically bind to antibodies, e.g., polyclonal or monoclonal antibodies, generated against an immunogen comprising a referenced amino acid sequence as described herein, an immunogenic fragment thereof, and/or a conservatively modified variant thereof.

As used herein, "endogenous FVIII" includes FVIII which originates from the mammal intended to receive treatment. The term also includes FVIII transcribed from a transgene or any other foreign DNA present in said mammal. As used herein, "exogenous FVIII" includes FVIII which does not originate from said mammal.

The FVIII molecule exists naturally and in therapeutic preparations as a heterogeneous distribution of polypeptides arising from a single gene product (see, e.g., Andersson et al., Proc. Natl. Acad. Sci. USA, 83, 2979 2983, May 1986). The term "Factor VIII" as used herein refers to all such polypeptides, whether derived from blood plasma or produced through the use of recombinant DNA techniques and include, but is not limited to FVIII mimetics, fc-FVIII conjugates, FVIII chemically modified with water soluble polymers and other forms or derivatives of FVIII. Commercially available examples of therapeutic preparations containing FVIII include those sold under the trade names of HEMOFILM and RECOMBINATE (available from Baxter Healthcare Corporation, Deerfield, Ill., U.S.A.). Other preparations comprise primarily a single subpopulation of FVIII molecules, which lack the B domain portion of the molecule.

The starting material of the present disclosure is FVIII, which can be derived from human plasma, or produced by recombinant engineering techniques, as described in patents U.S. Pat. Nos. 4,757,006; 5,733,873; 5,198,349; 5,250,421; 5,919,766; EP 306 968.

The FVIII molecules useful for the present disclosure include the full-length protein, precursors of the protein, biologically active or functional subunits or fragments of the protein, and functional derivatives thereof, as well as variants thereof as described herein below. Reference to FVIII is meant to include all potential forms of such proteins and wherein each of the forms of FVIII has at least a portion or all of the native B domain sequence intact.

Polynucleotides encoding a rFVIII of the disclosure include, without limitation, those that (1) specifically hybridize under stringent hybridization conditions to a nucleic acid encoding a referenced amino acid sequence as described herein, and conservatively modified variants thereof; (2) have a nucleic acid sequence that has greater than about 95%, about 96%, about 97%, about 98%, about 99%, or higher nucleotide sequence identity, over a region of at least about 25, about 50, about 100, about 150, about 200, about 250, about 500, about 1000, or more nucleotides (up to the full length sequence of 6996 nucleotides of the mature protein), to a reference nucleic acid sequence as described herein.

Variant (or analog) polypeptides include insertion variants, wherein one or more amino acid residues are added to an FVIII amino acid sequence of the disclosure. Insertions may be located at either or both termini of the protein, and/or may be positioned within internal regions of the FVIII amino acid sequence. Insertion variants, with additional residues at either or both termini, include for example, fusion proteins and proteins including amino acid tags or other amino acid labels. In one aspect, the FVIII molecule may optionally contain an N-terminal Met, especially when the molecule is expressed recombinantly in a bacterial cell such as *E. coli*.

In deletion variants, one or more amino acid residues in a FVIII polypeptide as described herein are removed. Deletions can be effected at one or both termini of the FVIII polypeptide, and/or with removal of one or more residues within the FVIII amino acid sequence. Deletion variants, therefore, include all fragments of a FVIII polypeptide sequence.

In substitution variants, one or more amino acid residues of a FVIII polypeptide are removed and replaced with alternative residues. In one aspect, the substitutions are conservative in nature and conservative substitutions of this type are well known in the art. Alternatively, the disclosure embraces substitutions that are also non-conservative. Exemplary conservative substitutions are described in Lehninger, [Biochemistry, 2nd Edition; Worth Publishers, Inc., New York (1975), pp.71-77]and set out immediately below.

Embodiments and additional aspects of the present invention will be described below. They can be combined freely unless the context clearly indicates otherwise.

In some embodiments, any deleted, substituted and/or other variation of the FVIII polypeptide may be processed without the need for further variation of the process itself. It's however relevant to the process that a FVIII polypeptide is processed, because it's specific to the resulting FVIII formulations that they comprise only a minor fraction of the actual FVIII polypeptide in comparison to the overall amount of constituents therein.

From that it's apparent that the process may be such that any potential damage to the FVIII polypeptide freeze-dried as a part of the formulation is avoided because a slight decrease of the FVIII polypeptide activity in the finally freeze-dried formulation results in an percentage wise huge impact of activity in the final product.

In some embodiments, the method further comprises the steps c), d) and e) after step b):
c) storing and homogenizing the freeze-dried pellets
d) assaying the freeze dried pellets while they are being stored and homogenized;
e) loading the freeze-dried pellets into containers.

The storing and homogenization step c) can also be performed in the rotating receptacle within the vacuum chamber used for freeze-drying. A statistically relevant number of samples are extracted for performing an assay. After that the optional separate storage container is packed into a sterile containment. After assaying the content of each storage container all necessary properties such as e.g. actives content are known. The filling process into the final containers with the user defined amounts of pellets can then begin. The storage containers are transferred to an isolated filling line and docked at a sterile docking station. The contents of the containers are transferred inside the isolator to the storage of the filling machine.

In another embodiment of the method, in step a) the droplets are formed by means of droplet formation of the solution by passing through frequency-assisted nozzles. Preferably the oscillating frequency is ≥1000 Hz to ≤2000 Hz.

Independent of the nozzle being frequency-assisted, the nozzle diameter can be in the range of from 100 μm to 500 μm, preferably in the range of from 200 μm to 400 μm, very preferably in the range of from 350 μm to 450 μm. Said nozzle diameters result in droplet sizes in the range from about 200 μm to about 1000 μm, preferably in the range of from about 400 μm to about 900 μm, very preferably in the range of from about 700 μm to 900 μm In this context a size of "about" means sizes of the resulting droplets being no more than ±30% deviating from the size mentioned with regard to the d90 value of the distribution. For example a resulting droplet size of about 400 μm is understood as the droplets that are produced varying in size between 280 μm and 520 μm with regard to the d90 value of the distribution.

The droplets formed display a certain droplet size distribution around a median value which should be about the one referenced to above.

In some embodiments, the nozzle is frequency-assisted and the variation around the median value is smaller. In some embodiments the meaning of "about" can be restricted to droplets being no more than ±30% deviating from the size mentioned.

In the example referred to just above a resulting droplet size of about 400 μm can then be understood as the droplets that are produced varying in size between 280 μm and 520 μm with regard to the d90 value of the distribution. In view of the below described effects passing the droplets through a frequency-assisted nozzle is thus of further advantage to further lower potential negative impact on the final freeze-dried pellets.

Generally droplets of the sizes given above are of advantage, as it was found that the subsequent steps b) to e) can be performed with a higher yield in FVIII activity.

Without being bound to that, it's hypothesized that smaller droplets freeze too quickly in the freeze-drying step b) due to the much bigger surface to volume ratio and that the fragile FVIII polypeptide is thereby partially destroyed. Furthermore smaller droplets result in smaller pellets which have an increased tendency to become electrostatically charged, while the latter impairs with later handling of such pellets. Bigger droplets do not freeze homogenously resulting in partial destruction of the FVIII polypeptide at the outer shell of the freeze-dried pellet and incomplete freeze-drying of the inner compartment of the droplets with resulting partial destruction of the FVIII polypeptide during storage.

In another embodiment of the method, in step a) the inner surface of the cooling tower has a temperature of not warmer than −120° C., preferably ≥−150° C. to ≤−120° C. Preferably the temperature is ≥−140° C. to ≤−130° C.

The above referred to temperatures of ≥−140° C. to ≤−130° C. are optimized for droplet sizes in the range of about ≥700 μm to about ≤900 μm that are frozen while falling a distance of 3m to 4m.

As long as the temperature is kept below −120° C. on the inner surface of the cooling tower, the beneficial results of some embodiments can be obtained by adjustment of falling distance and droplet size.

In some embodiments, the inner surface of the cooling tower is cooled by passing a coolant through one or more pipes which are in thermal contact with the inner surface. The coolant may be liquid nitrogen or nitrogen vapor of a desired temperature.

In some embodiments, a target dosage is established for factor VIII, the assay in step d) determines the active content of factor VIII in the freeze-dried pellets and the containers are loaded with an amount of freeze-dried pellets that provides a dosage which equals the target dosage, or exceeds the target dosage by ≤25%. Preferably the target dosage is exceeded by ≤10%, more preferably by ≤5%.

It is a direct result of some embodiments allowing a gentle freezing of the FVIII polypeptide that allows not to dramatically exceed the target dosage upon filling, because the process does not decrease the activity of the FVIII polypeptide.

In some embodiments, the pellets obtained in step a) have a maximum of the particle size distribution d50 of about ≥200 μm to about ≤1500 μm. Preferred is a maximum of the particle size distribution d50 of about ≥700 μm to about ≤900 μm.

Pellets of smaller size than 200 μm are less favorable as in those pellets freezing would be faster which may result in damages of the freeze dried polypeptide and thus loss in potency requiring higher target dosage. Furthermore electrostatic influences of the resulting powder increase dramatically at sizes below 200 μm leading to inferior handling properties of the product of the present process, and yield losses due to entrapment of pellets in water vapor can be expected.

Increase of pellet size to more than 1500 μm may endanger complete freezing of the pellet in the described setup and thus impair the overall efficacy of a later product.

In some embodiments, the solution comprising factor VIII in step a) has a content of dissolved solids of ≥8 weight-% to ≤12 weight-%. Preferred is a content of dissolved solids of ≥9 weight-% to ≤11 weight-%.

In principle higher loads of dissolved solids of about 15 to 20 weight-% would be deemed favorable in processes of the kind concerned herein because the resulting pellets would normally be expected to be frozen more easily and dried more robustly.

However, in the present case the above ranges are found to be better as the handled solid (comprising FVIII) later needs to be reconstituted and injected into a human being which (at higher loads) would either result in an incompatible osmolality of the injection solution resulting in potential tissue damage and/or injection pain or otherwise would require significantly higher reconstitution volumes to avoid that which in fact renders the solution no longer practically injectable.

In some embodiments, the solution comprising factor VIII in step a) has the following composition with respect to 1 gram of the solution, the balance being water for injection:

Factor VIII ≥99 IU to ≤101 IU,
Sucrose ≥68 mg to ≤72 mg, preferably ≥70 mg to ≤71.8 mg
Histidine ≥2 mg to ≤4 mg, preferably ≥3 mg to ≤3.8 mg
Glycine ≥23 mg to ≤26 mg, preferably ≥23.5 mg to ≤25.7 mg
NaCl ≥1 mg to ≤3 mg, preferably ≥1.5 mg to ≤2.5 mg
$CaCl_2$ >0.2 mg to <0.4 mg, preferably ≥0.25 mg to ≤0.35 mg
Polysorbate 80≥0.07 mg to ≤0.1 mg, preferably ≥0.075 mg to ≤0.095 mg

BRIEF DESCRIPTION OF THE DRAWINGS

The present invention will be further described with reference to the following figures and examples without wishing to be limited by them.

FIG. 1 schematically shows an apparatus for the method according to some embodiments;

FIG. 2 shows the temperature profile over time in a cooling tower according to some embodiments;

FIG. 3 shows a temperature and pressure profile during a freeze-drying step according to some embodiments;

FIG. 4 shows another temperature and pressure profile during a freeze-drying step according to some embodiments;

FIG. 5 shows the potency development of samples after different times of storage at room temperature (RT) or at 2-8° C.

FIG. 6 shows the product aggregate/fragment distribution of samples after different times of storage at room temperature (RT) or at 2-8° C. according to some embodiments;

FIG. 7 shows a Scanning Electron Microscopy (SEM) picture of a pellet produced according to some embodiments in 200-fold magnification;

DETAILED DESCRIPTION OF THE INVENTION

Figure 1:
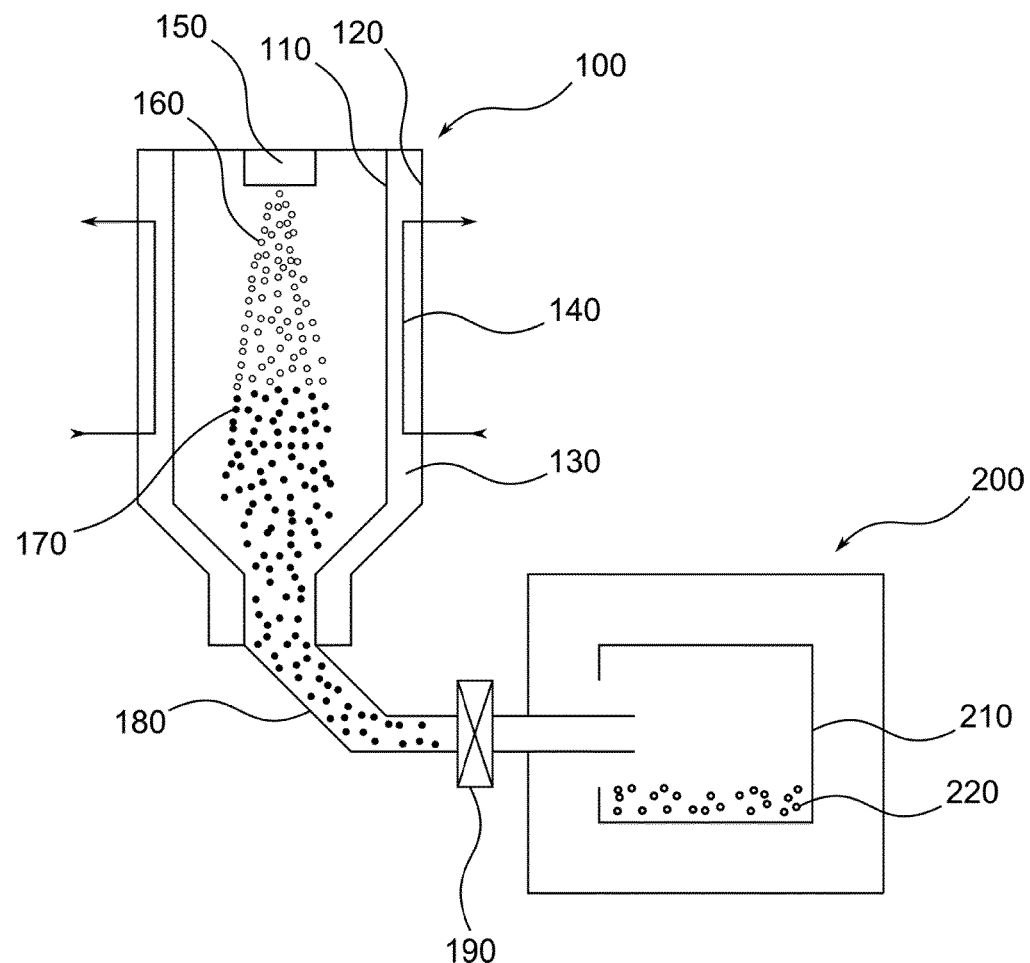
Figure 2:
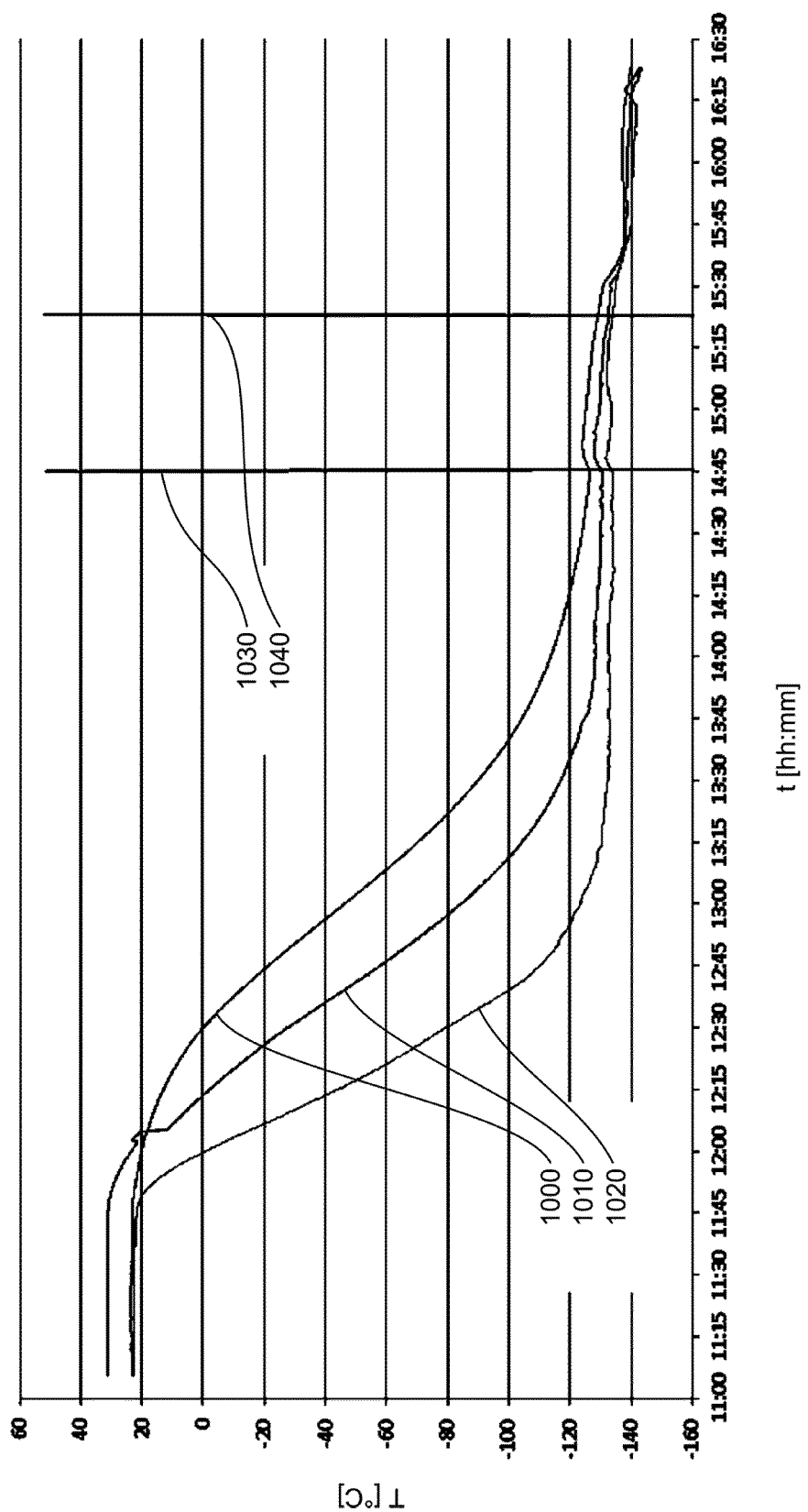
Figure 3:
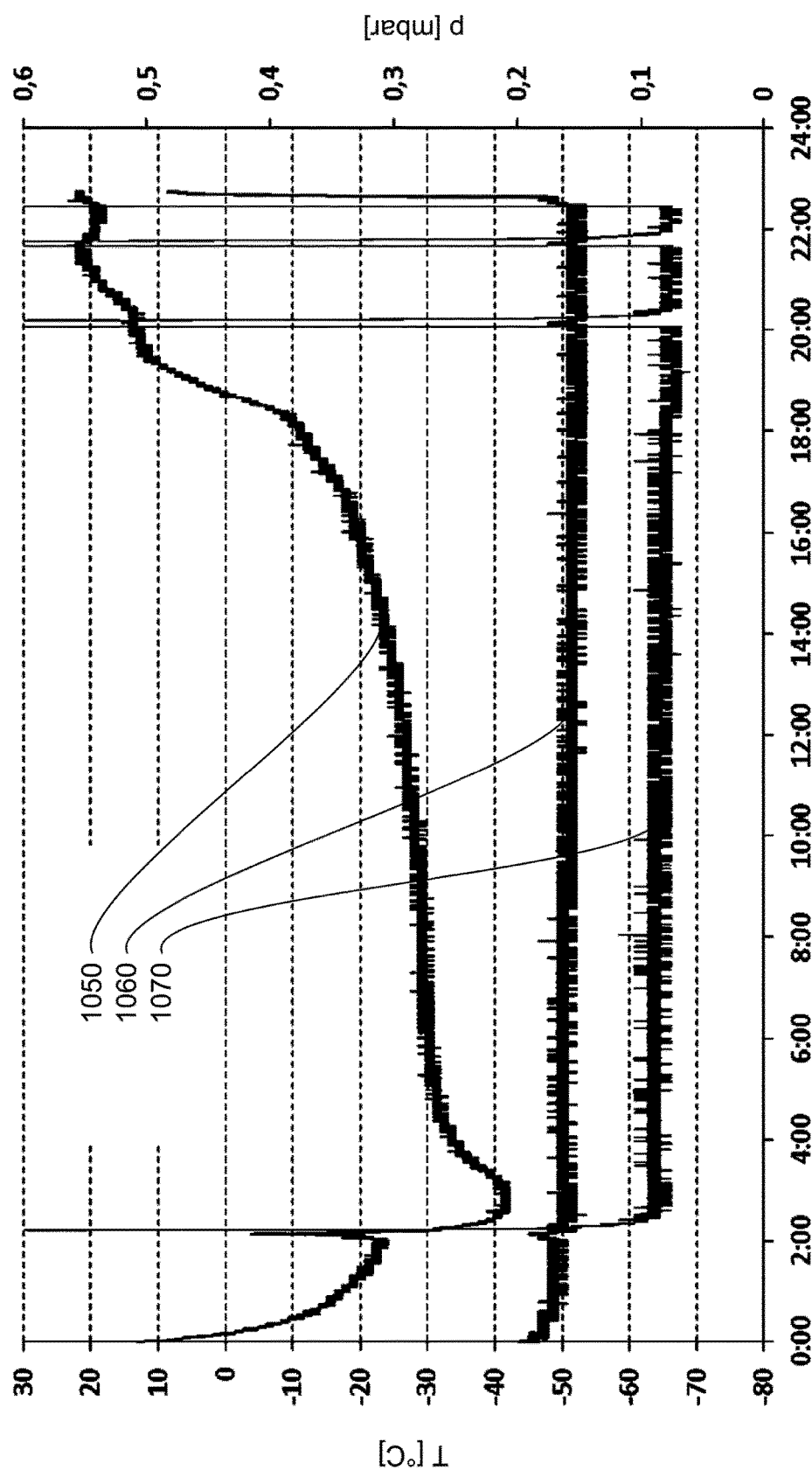
Figure 4:
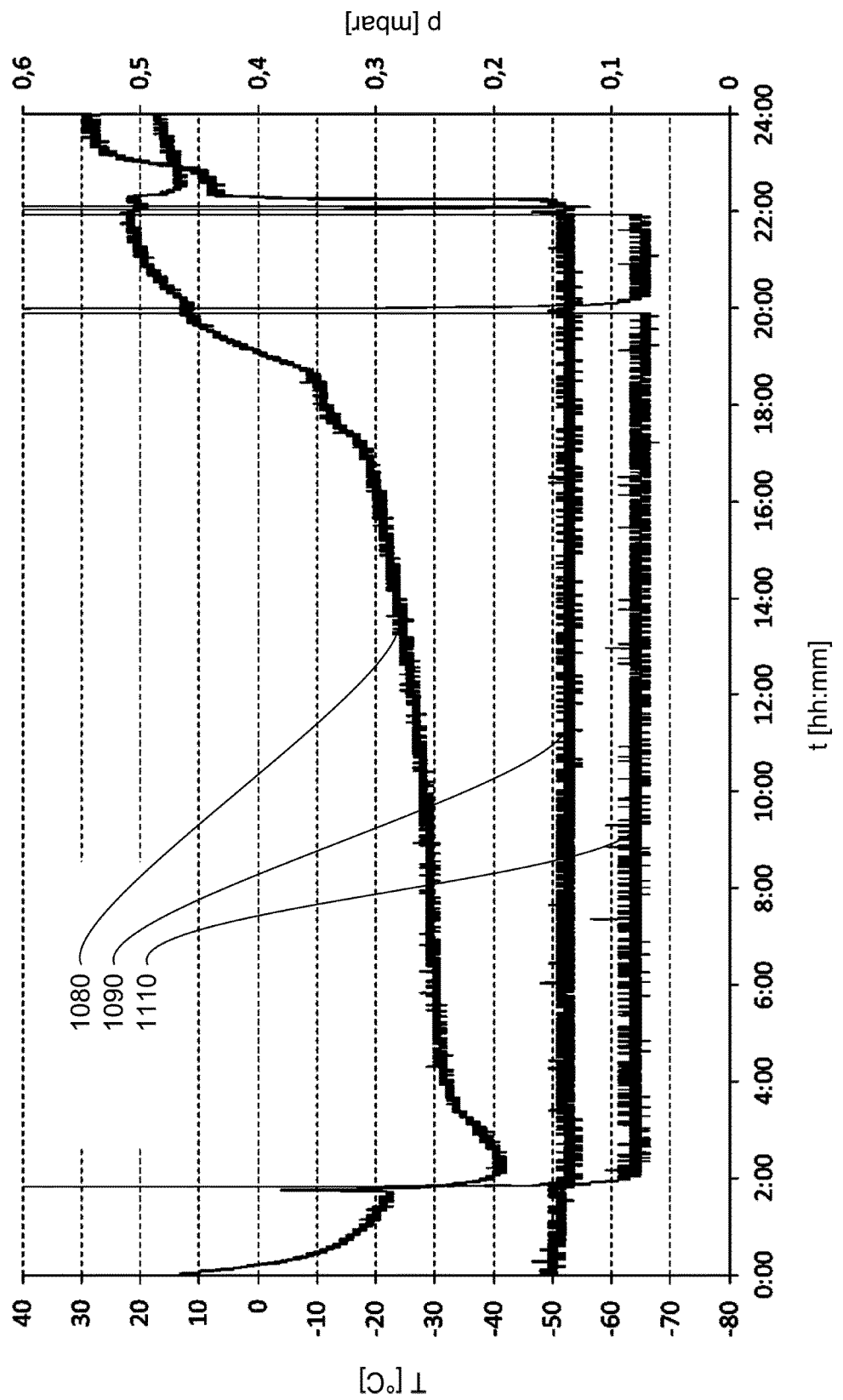
Figure 5:
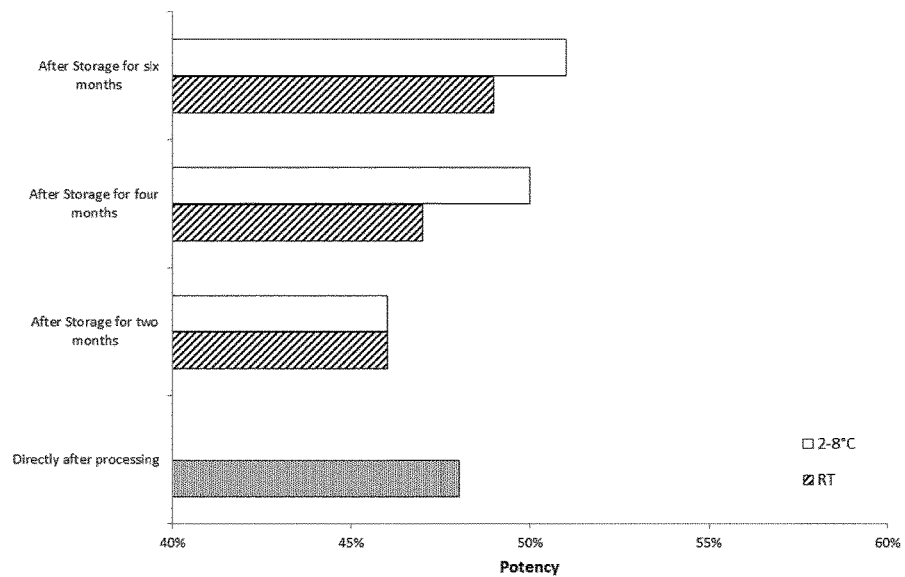
Figure 6:
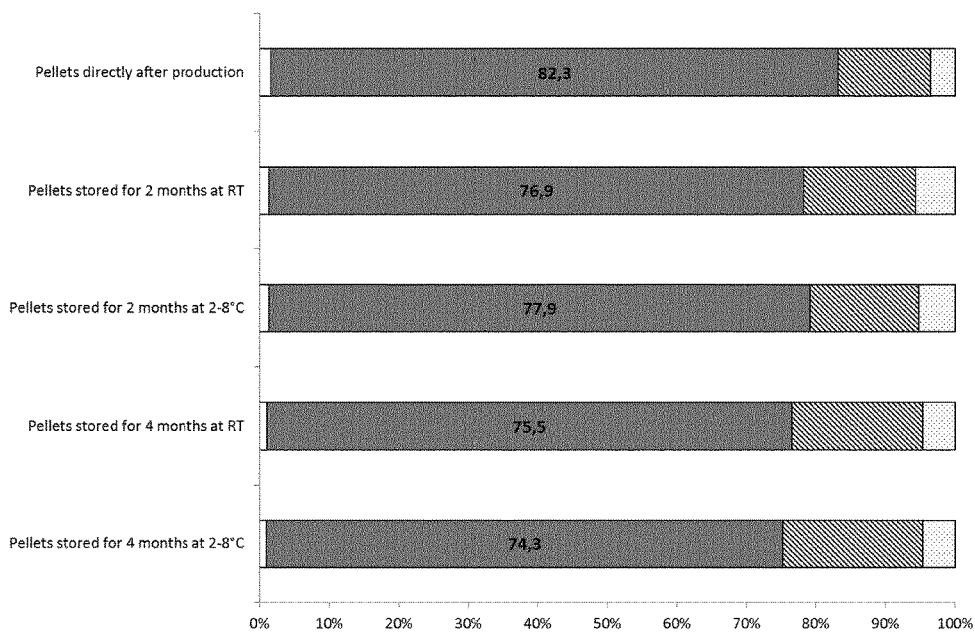
Figure 7:
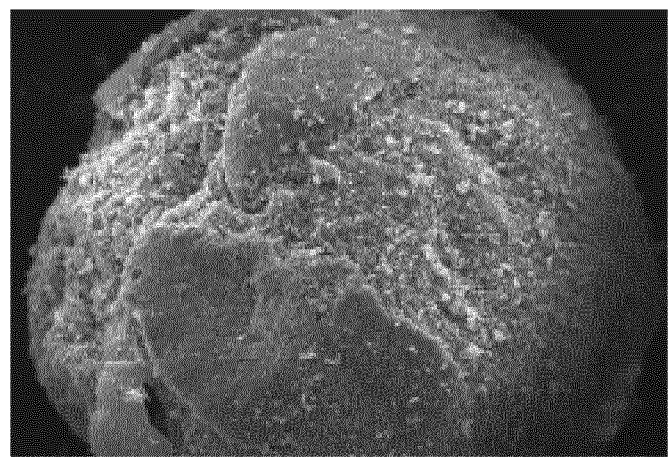
Figure 8:
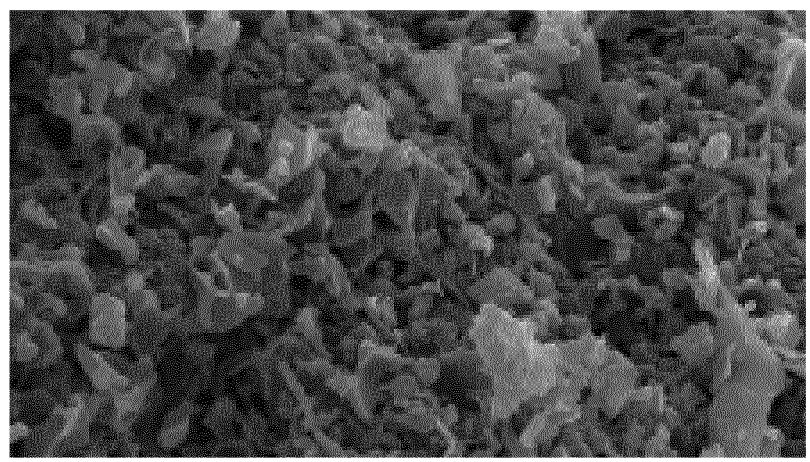
FIG. 8 shows a Scanning Electron Microscopy (SEM) picture of a pellet produced according to some embodiments in 2000-fold magnification.
Figure 9:
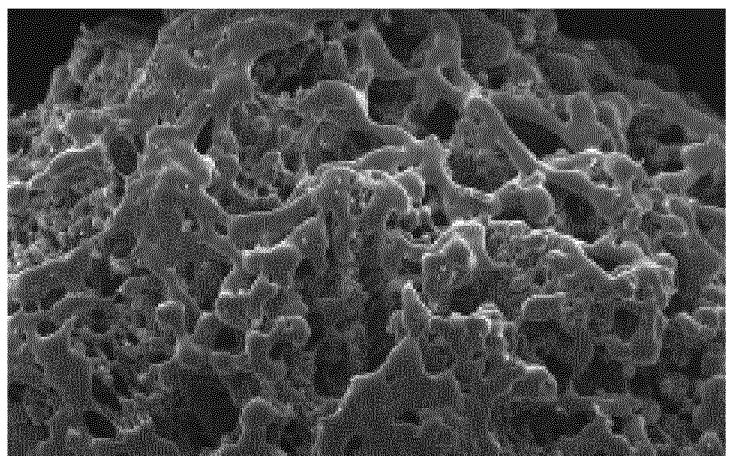
FIG. 9 shows a Scanning Electron Microscopy (SEM) picture of a pellet produced according to the method described in WO 2006/008006 A1 in 200-fold magnification.
Figure 10:
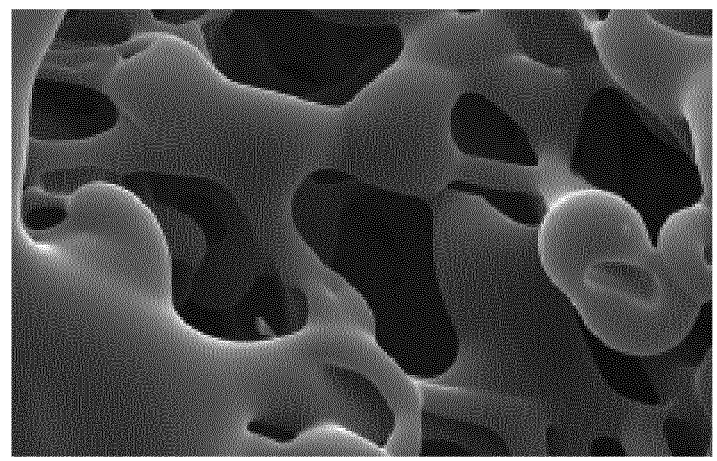
FIG. 10 shows a Scanning Electron Microscopy (SEM) picture of a pellet produced according to the method described in WO 2006/008006 A1 in 2000-fold magnification.
Figure 11:
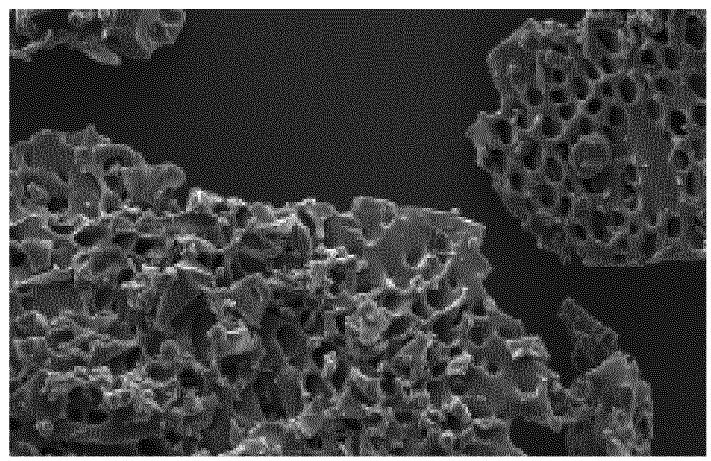
FIG. 11 shows a Scanning Electron Microscopy (SEM) picture of a lyophilisate produced according to standard lyophilisation in 200-fold magnification.
Figure 12:
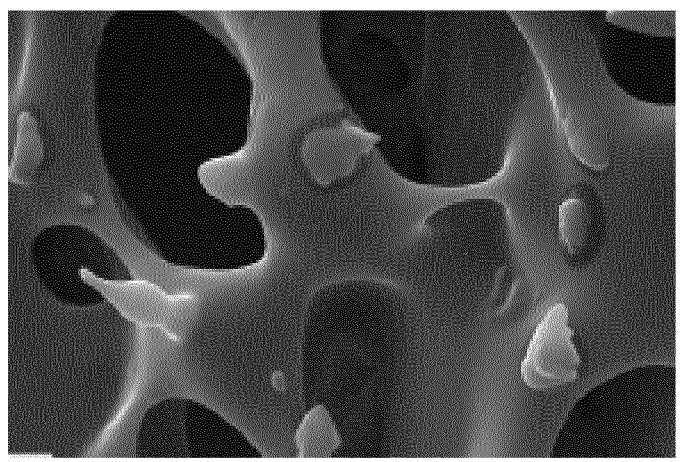
FIG. 12 shows a Scanning Electron Microscopy (SEM) picture of a lyophilisate produced according to standard lyophilisation in 2000-fold magnification.

FIG. 1 schematically depicts an apparatus for conducting the method according to some embodiments. The apparatus comprises, as main components, the cooling tower 100 and the vacuum drying chamber 200. The cooling tower comprises an inner wall 110 and an outer wall 120, thereby defining a space 130 between the inner wall 110 and the outer wall 120.

This space 130 houses a cooling means 140 in the form of piping. A coolant can enter and leave the cooling means 140 as indicated by the arrows of the drawing.

Coolant flowing through the cooling means 140 leads to a cooling of the inner wall 110 and thus to a cooling of the interior of the cooling tower 100. In the production of frozen pellets (cryopellets), liquid is sprayed into the cooling tower via nozzle 150. Liquid droplets are symbolized in accordance with reference numeral 160.

The liquid droplets eventually solidify (freeze) on their downward path, which is symbolized in accordance with reference numeral 170. Frozen pellets 170 travel down a chute 180 where a valve 190 permits entry into the vacuum drying chamber 200.

While not depicted here, it is of course also possible and even preferred that the chute 180 is temperature-controlled in such a way as to keep the pellets 170 in a frozen state while they are collecting before the closed valve 190.

Inside the vacuum drying chamber 200 a rotatable drum 210 is located to accommodate the frozen pellets to be dried. The rotation occurs around the horizontal axis in order to achieve an efficient energy transfer into the pellets. Heat can be introduced through the drum or via an encapsulated infrared heater. As an end result, freeze-dried pellets symbolized by the reference numeral 220 are obtained.

EXAMPLES

General—Determination of Potency the rFVIII Drug Product

Potency has been measured by the use of a Chromogenic assay using the Coatest™ FVIII kit. The chromogenic assay method consists of two consecutive steps where the intensity of color is proportional to the Factor VIII activity. In the first step, Factor X is activated to Factor Xa by Factor IXa with its cofactor, Factor VIIIa, in the presence of optimal amounts of calcium ions and phospholipids, with 5 minutes incubation at 37° C. Excess amounts of Factor X are present such that the rate of activation of Factor X is solely dependent on the amount of Factor VIII. In the second step, Factor Xa hydrolyzes the chromogenic substrate to yield a chromophore and the color intensity is read photometrically at 405 nm. The validity of the assay is confirmed using a linear regression statistical method against a standard of established potency and the potency of an unknown sample is calculated. Potency is reported in International Units per mL (IU/mL). In case potency is hereinafter referred to as a value of [%], such value is consistently to be understood as a percentage of a "target potency" in UI/ml (normalized values). Obviously bigger values of %-potency are preferred.

General—Size Exclusion Chromatography (SEC) to Determine Distribution of Product Fragments/Aggregates The principle components of rFVIII preparations are separated into regions based on their hydrodynamic volume, or molecular size on a TSK gel G4000SWXL column with dimensions 7.8 mm ID×30 cm, 8 mm particle size; 450 Angstrom pore size.

They are then quantitated based on their fluorescence emission at 340 nm after excitation at 276 nm. Quantitative results are expressed as relative % peak area for these regions. The procedure reports results for specific regions of the chromatogram and is used to measure rFVIII aggregates and integrity of chains.

Three regions (Region 1, Region 2, and Region 3) are determined, while Region 2 (in % of total sample) is desired to be maximum, as therein all rFVIII molecules not being aggregated nor fragmented are summarized.

General—Specific Surface Area According to BET

Determination of the specific surface via BET was performed in a multi-point measurement (nitrogen adsorption at 77 Kelvin) and for each sample, two independent amount of material were filled into BET containers and analyzed separately. The containers were tightly closed with stoppers, transferred to the sample preparation station, evacuated and pre-treated for 16 h at 30° C. in vacuum (<0.2, bar) to remove volatile components. Subsequently the samples were vented with nitrogen, weighed and measured according to DIN ISO 9277 using nitrogen.

General—Scanning Electron Microscopy (SEM) Measurements

Preparation of samples was performed in a glove bag under nitrogen atmosphere, each sample was prepared individually. The sample was placed on a holder and sputtered with gold. Subsequently the scanning electron microscopy measurement was performed.

Example 1

Cryopellets of a solution of Kogenate® PF were manufactured. Kogenate® PF is a plasma protein-free recombinant human factor VIII. The formulation for 1 g of the solution is given below:

| Solids | Target: 10% | Actual: 10.3% |
|---|---|---|
| Kogenate ® PF | 100 IU | 100 IU |
| Sucrose | 70.87 mg | 71.79 mg |
| Histidine | 3.32 mg | 3.59 mg |
| Glycine | 23.6 mg | 25.54 mg |
| Sodium chloride | 1.88 mg | 2.03 mg |
| Calcium chloride | 0.28 mg | 0.30 mg |

-continued

| Solids | Target: 10% | Actual: 10.3% |
|---|---|---|
| Polysorbate 80 | 0.08 mg | 0.09 mg |
| Water for injection | ad 1 g | ad 1 g |

The bulk solution was sprayed into a wall-cooled cooling tower in accordance with the method of some embodiments. The spraying nozzle had one aperture with a diameter of 400 µm. This corresponds to target droplet size of 800 µm. The oscillation frequency was 1375 Hz, the deflection pressure 0.2 bar and the pump was operated at 22 rpm. After a total duration of 35 minutes 879.3 g of frozen pellets were collected (96% yield).

The interior temperatures of the cooling tower were monitored and their development over time is depicted in FIG. 2. Curve 1000 represents the sensor reading from an upper part of the cooling tower, curve 1010 the sensor reading from a central part of the cooling tower and curve 1020 the sensor reading from a lower part of the cooling tower. At 14:45 o'clock, when the temperatures had reached −126.0° C. (upper sensor), −129.7° C. (central sensor) and −133.1° C. (lower sensor), the spraying operation was initiated. This is represented by mark 1030 in FIG. 2. At 15:20 o'clock the spraying operation was halted (mark 1040) with recorded temperatures of −130.7° C. (upper sensor), −133.5° C. (central sensor) and −135.2° C. (lower sensor). The frozen pellets were collected in a cooled container having a temperature between −55° C. and −53° C.

Example 2

This example concerns the freeze-drying of a sample of cryopellets obtained in example 1. A LyoMotion freeze-dryer from Meridion was employed in this step. This machine comprises a rotating drum in which the cryopellets were agitated and subjected to drying.

A total of 21.3 g freeze-dried pellets (72.6% yield) having a residual moisture of 0.95% were isolated.

The temperature and pressure profiles of the freeze-drying step are shown in FIG. 3. Curve 1050 represents the product temperature, curve 1060 the condenser temperature of the freeze-drying machine and curve 1070 the internal pressure inside the vacuum chamber of the freeze-drying machine.

Example 3

This example concerns the freeze-drying of another sample of cryopellets obtained in example 1. A LyoMotion freeze-dryer from Meridion was employed in this step. This machine comprises a rotating drum in which the cryopellets were agitated and subjected to drying.

A total of 21.4 g freeze-dried pellets (73.7% yield) having a residual moisture of 0.70% were isolated.

The temperature and pressure profiles of the freeze-drying step are shown in FIG. 4. Curve 1080 represents the product temperature, curve 1090 the condenser temperature of the freeze-drying machine and curve 1100 the internal pressure inside the vacuum chamber of the freeze-drying machine.

Results

Potency assays and size exclusion chromatography analyses of the products obtained are given in the table below for samples taken from the process directly after manufacturing.

| | Potency [% of | Size exclusion chromatography (average of 2 samples) [relative area-%] | | |
|---|---|---|---|---|
| Sample | target potency] | Region 1 (HMW) | Region 2 | Region 3 |
| Ex. 2 | 86.2% | 0.6 | 75.0 | 17.2 |
| Ex. 2 | 89.9% | 0.5 | 74.6 | 17.5 |
| Ex. 3 | 87.9% | 0.5 | 73.8 | 18.3 |
| Ex. 3 | 88.4% | 0.5 | 74.5 | 17.6 |

Two samples from each example were analyzed with respect to the potency of the factor VIII therein. Target potencies were 250.0 mg/vial. A loss of potency during the processing of the bulk solution and freeze-drying is to be expected. The determined actual potencies between 86.2% and 89.9% were considerably lower in variation than those observed in conventional freeze-drying in a vial. Here potencies ranging from 80.9% to 91.2% can be observed depending on the position of the individual vial in the drying chamber.

For reference, the following table gives analytical data for the precursors of examples 2 and 3 (IPC values).

| | Target | Potency [% of | Size exclusion chromatography (average of 2 samples) [relative area-%] | | |
|---|---|---|---|---|---|
| Sample | potency [IU/ml] | target potency] | Region 1 (HMW) | Region 2 | Region 3 |
| Kogenate ® PF solution after thawing | 1220.0 | 101.2% | 0.4 | 74.5 | 17.6 |
| Kogenate ® PF bulk solution after dilution | 100.0 | 96.8% | 0.6 | 73.6 | 17.5 |
| Ex. 1 (cryopellets) | 100.0 | 111.7% | 0.6 | 73.0 | 18.0 |

Furthermore the above properties of the samples were evaluated for up to 6 months of storage at room temperature (RT) and at 2-8° C.

It can be seen from FIG's 5 and 6 (samples were prepared from different starting material of lower activity) that no significant changes in potency or fragment/aggregate composition of the samples has occurred, which underlines the robustness of the process according to some embodiments with regard to the properties of the thereby produced pellets.

Example 4

Direct Comparison to the Prior Art

Solutions of the identical batch of Factor VIII drug substance with the same formulation composition as provided in Example 1 were prepared and processed via different drying methods. 3000 ml solution were frozen in a cooling tower according to Example 1, and the frozen pellets were lyophilized in two different rotary freeze dryers (LyoMotion) with a batch size of 319 g and 2614 g.

A separate part of the solution was processed according to the method described in WO 2006/008006 A1. A total of 1200 ml solution were sprayed in portions of 200 ml through a 400 µm nozzle and atomized at a frequency of 900 Hz with a rate of about 16.5 g/min. The droplets were frozen in an isolated vessel filled with liquid nitrogen that was positioned approx. 25 cm below the nozzle and stirred throughout the process. After completion of spraying each portion, the frozen pellets were removed by pouring the liquid nitrogen through a pre-cooled sieve and storing them at low temperature. Once all portions were collected, they were placed in 2 racks lined with plastic foil onto the pre-cooled shelved of a Virtis Advantage Pro freeze dryer and lyophilized. Primary drying was conducted at −10° C. shelf temperature over a duration of 60 hours, followed by secondary drying for 8 hours at 25° C. After completion of drying, the dry pellets were instantly transferred into glass bottles and firmly closed. Subsequently, 250 mg of pellets were weighed into 10R type I glass vials under a nitrogen atmosphere.

A third separate part of the solution was filled into 10R type I glass vials and freeze dried in a conventional vial freeze dryer. A total of 488 vials were filled with 2.5 ml solution per vial (1241 g solution in total), semi-stoppered and loaded into a HOF freeze dryer. The solution was frozen to −45° C., and primary drying was performed at −20° C., followed by a secondary drying step at 25° C. The complete freeze drying process required approx. 65 hours. The vials were stoppered within the freeze dryer and sealed directly after unloading.

All three samples—those from the first processing according to Example 1, those processed as described in WO 2006/008006 A1 and those from a conventional vial freeze drying process—where thereafter made subject to specific surface area according to BET and Scanning Electron Microscopy (SEM) measurements.

It can be seen that the pellets produced pursuant to some embodiments display a higher specific surface area—which improves reconstitution of the freeze-dried solid in a liquid for administration—and more homogeneous morphology, which improves handling properties in later process steps for those pellets.

The respective specific surface area according to BET are summarized as follows:

| Pellet produced . . . | Specific surface area according to BET [m$^2$/g] |
|---|---|
| according to embodiments disclosed herein | 5.2 |
| according to WO 2006/008006 A1 | 0.8 |
| standard lyophilisation | 0.4 |

It's apparent that the specific surface area of pellets that are produced by some embodiments disclosed herein is significantly bigger than that of pellets produced according to similar prior art processes (such as WO 2006/008006 A1) and particularly compared to standard lyophilisation.

The invention claimed is:

1. A method for the production of freeze-dried pellets comprising factor VIII, the method comprising the steps of:
    a) freezing droplets of a solution comprising factor VIII to form pellets; and
    b) freeze-drying the pellets to produce freeze-dried pellets comprising factor VIII,
    wherein the droplets in step a) are formed by droplet formation, wherein the solution comprising factor VIII is sprayed into a cooling tower comprising a temperature-controllable inner wall surface and an interior temperature below a freezing temperature of the solution, and
    wherein in step b) the pellets are freeze-dried in a rotating receptacle, wherein the rotating receptacle is housed inside a vacuum chamber.

2. The method of claim 1, further comprising
    c) storing and homogenizing the freeze-dried pellets comprising factor VIII;
    d) assaying the freeze-dried pellets comprising factor VIII while they are being stored and homogenized; and
    e) loading the freeze-dried pellets comprising factor VIII into containers.

3. The method of claim 1, wherein freezing droplets of a solution comprising factor VIII to form pellets comprises passing the solution comprising factor VIII through frequency-assisted nozzles.

4. The method of claim 3, wherein an oscillating frequency of the frequency-assisted nozzles is ≥1000 Hz and ≤2000 Hz.

5. The method of claim 1, wherein the inner wall surface of the cooling tower comprises a temperature of ≤−120° C.

6. The method of claim 1, wherein the inner wall surface of the cooling tower is cooled by passing a coolant through one or more pipes, wherein the one or more pipes are in thermal contact with the inner surface.

7. The method of claim 2,
    wherein factor VIII of the freeze-dried pellets comprising factor VIII comprises a target dosage,
    wherein assaying the freeze-dried pellets comprising factor VIII while they are being stored and homogenized comprises determining an active content of factor VIII in the freeze-dried pellets comprising factor VIII, and
    wherein loading the freeze-dried pellets comprising factor VIII into containers comprises loading an amount of freeze-dried pellets comprising factor VIII into the containers such that a dosage of factor VIII in the amount of freeze-dried pellets comprising factor VIII equals or exceeds the target dosage by ≤25%.

8. The method of claim 1, wherein the pellets of step a) comprise a maximum of the particle size distribution d50 of ≥200 μm to ≤1500 μm.

9. The method of claim 1, wherein the solution comprising factor VIII in step a) comprises a content of dissolved solids of ≥8 weight-% and ≤12 weight-%.

10. The method of claim 1, wherein 1 gram of the solution comprising factor VIII in step a) comprises the following composition, the balance being water for injection:

| Factor VIII | ≥99 IU to ≤101 IU |
|---|---|
| Sucrose | ≥68 mg to ≤72 mg |
| Histidine | ≥2 mg to ≤4 mg |
| Glycine | ≥23 mg to ≤26 mg |
| NaCl | ≥1 mg to ≤3 mg |
| CaCl$_2$ | ≥0.2 mg to ≤0.4 mg |
| Polysorbate 80 | ≥0.07 mg to ≤0.1 mg. |

* * * * *